United States Patent
Spinelli

(10) Patent No.: US 11,877,993 B1
(45) Date of Patent: Jan. 23, 2024

(54) GAMMA-HYDROXYBUTYRATE SALTS FOR THE TREATMENT OF PSYCHOLOGICAL DISORDERS

(71) Applicant: Kelly Kathleen Spinelli, Bonita Springs, FL (US)

(72) Inventor: Kelly Kathleen Spinelli, Bonita Springs, FL (US)

( * ) Notice: Subject to any disclaimer, the term of this patent is extended or adjusted under 35 U.S.C. 154(b) by 29 days.

(21) Appl. No.: 17/847,860

(22) Filed: Jun. 23, 2022

Related U.S. Application Data

(60) Provisional application No. 63/213,907, filed on Jun. 23, 2021.

(51) Int. Cl.
  *A61K 31/19* (2006.01)
  *A61P 25/22* (2006.01)

(52) U.S. Cl.
  CPC .............. *A61K 31/19* (2013.01); *A61P 25/22* (2018.01)

(58) Field of Classification Search
  CPC ..................................................... A61K 31/19
  See application file for complete search history.

(56) References Cited

U.S. PATENT DOCUMENTS

| | | |
|---|---|---|
| 8,591,922 B1 | 11/2013 | Allphin et al. |
| 8,901,173 B2 | 12/2014 | Allphin et al. |
| 9,132,107 B2 | 9/2015 | Allphin et al. |
| 10,195,168 B2 | 2/2019 | Allphin et al. |
| 10,675,258 B2 | 6/2020 | Allphin et al. |

OTHER PUBLICATIONS

Schwartz ("Gamma hydroxy butyric acid and sodium oxybate used to treat posttraumatic stress disorder," CNS Spectrums, 2007, vol. 12, No. 12, 884-886).*
Xywav—Dosing and Titration Gide Including EMR integration and e-Prescribing, Aug. 1, 2021, Jazz Pharmaceuticals, 59 pp.

* cited by examiner

*Primary Examiner* — Yong S. Chong
(74) *Attorney, Agent, or Firm* — Kaplan Breyer Schwarz, LLP

(57) ABSTRACT

A method of treating PTSD and/or other psychological disorders comprises administering at least one gamma-hydroxybutyrate salt.

3 Claims, No Drawings

GAMMA-HYDROXYBUTYRATE SALTS FOR THE TREATMENT OF PSYCHOLOGICAL DISORDERS

STATEMENT OF RELATED CASES

This case claims priority of U.S. Pat. App. Ser. 63/213,907 filed Jun. 23, 2021 and incorporated by reference herein

FIELD OF THE INVENTION

This disclosure relates to the use of gamma-hydroxybutyrate salts, derivatives, or related compounds in pharmaceutical compositions and formulations.

BACKGROUND OF THE INVENTION

Post-traumatic stress disorder (PTSD) is a mental disorder that can develop in response to exposure to a traumatic event. Symptoms may include disturbing thoughts, feelings, or dreams related to the events, mental or physical distress to trauma-related cues, attempts to avoid trauma-related cues, alterations in the way a person thinks and feels, and an increase in the fight-or-flight response. The overall lifetime prevalence of PTSD in the United States is approximately 8 to 9 percent.

PTSD is marked by altered autonomic response (heart rate, skin conductance) and facial electromyography (EMG) reactivity to external, trauma-related stimuli as well as to internal, mental imagery of a traumatic event. Reactivity to trauma-related cues correlates with severity of the disorder. Patients with PTSD show increased startle and heightened heart-rate responses to startling stimuli. Functional neuroimaging studies using positron emission tomography (PET) or functional magnetic resonance imaging (fMRI) in individuals with PTSD have shown altered activity in the amygdala as well as in the hippocampus and insular cortex (Pitman et al. *Nat Rev Neurosci.* 2012, 13:769-787).

Common comorbid diagnoses with PTSD are anxiety disorders, other trauma-related disorders and stressor-related disorders, and even depressive disorders. Individuals with PTSD who report high negative affectivity and low positive affectivity are more likely to have a comorbid diagnosis of depression. In patients who have PTSD, the risk of almost all anxiety disorders is increased markedly (Brady et al. J Clin Psychiatry. 2000, 61:22-32).

The treatment of patients with PTSD relies on a multidimensional approach. Treatment options include patient education, social support, and anxiety management through psychotherapy and psychopharmacologic intervention. Studies demonstrate that cognitive-behavior treatment is effective in ameliorating the symptoms of PTSD. Selective serotonin reuptake inhibitors are the mainstay of pharmacologic treatment.

Recent studies have suggested alternative pharmacological interventions for PTSD with comorbid psychological disorders. Mitchell et al. tested the efficacy and safety of 3,4-methylenedioxymethamphetamine (MDMA)-assisted therapy for the treatment of patients with severe PTSD, including those with common comorbidities such as dissociation, depression, a history of alcohol and substance use disorders, and childhood trauma (Mitchell et al. *Nat Med* 2021). MDMA was found to induce significant and robust attenuation in CAPS-5 score compared with placebo (P<0.0001, d=0.91) and to significantly decrease the SDS total score (P=0.0116, d=0.43). MDMA-assisted therapy was thus found to be efficacious and well-tolerated in individuals with severe PTSD, even in those with comorbidities. The efficacy of other scheduled psychoactive compounds in the treatment of PTSD and other psychological disorders is an active focus of clinical investigation.

SUMMARY

This disclosure relates to the use of one or more gamma-hydroxybutyrate salts in the treatment of psychological disorders, including trauma and stressor-related disorders, such as post-traumatic stress disorder (PTSD), anxiety disorders, obsessive compulsive and related disorders.

Some embodiments of the invention provide a method for treating a patient with a psychological disorder, wherein the method comprises administering to the patient one or more gamma-hydroxybutyrate salts. Some embodiments in accordance with the invention provide for the use of a medicament comprising one or more gamma-hydroxybutyrate salts for the treatment of a psychological disorder. The psychological disorders treatable by methods in accordance with the invention include, among any others, those selected from the group consisting of: trauma- and stressor-related disorders (notably but not exclusively PTSD), anxiety disorders (including panic disorders), and obsessive-compulsive and related disorders.

In some embodiments, the gamma-hydroxybutyrate salts comprise one or more of calcium oxybate, magnesium oxybate, potassium oxybate, sodium oxybate, in any combination.

Gamma-hydroxybutyrate, or γ-hydroxybutyric acid or GHB, is a naturally occurring neurotransmitter and a Schedule III substance. However, salts of gamma-hydroxybutyric acid, such as sodium oxybate, are approved in the United States and other jurisdictions for the medical treatment of cataplexy associated with narcolepsy and excessive daytime sleepiness (EDS) associated with narcolepsy.

U.S. Pat. No. 8,591,922B1, U.S. Pat. No. 9,132,107B2, U.S. Pat. No. 8,901,173B2, U.S. Ser. No. 10/195,168B2, and U.S. Ser. No. 10/675,258B2 (all incorporated herein by reference) describe pharmaceutical compositions and formulations comprising mixed salts of gamma-hydroxybutyrate (GHB), methods of making the pharmaceutical compositions and formulations, and methods of their use for the treatment of sleep disorders such as apnea, sleep time disturbances, narcolepsy, cataplexy, sleep paralysis, hypnagogic hallucination, sleep arousal, insomnia, and nocturnal myoclonus.

Some embodiments of the invention provide a method for treating a patient having a psychological disorder, comprising administering to the patient of an effective amount of a pharmaceutical composition including one or more gamma-hydroxybutyrate salts.

Some embodiments of the invention provide a method of treating a patient having a psychological disorder, comprising orally administering to the patient a pharmaceutical composition comprising a mixture of four salts of gamma-hydroxybutyrate, wherein the mixture comprises a calcium salt of gamma-hydroxybutyrate, a magnesium salt of gamma-hydroxybutyrate, a potassium salt of gamma-hydroxybutyrate, and a sodium salt of gamma-hydroxybutyrate, and wherein the salts are present in a wt/wt % ratio of about 47%:19%:26%:8%, respectively.

Some embodiments of the invention provide a method of treating a patient having a psychological disorder, comprising orally administering to the patient a pharmaceutical composition comprising a mixture of four salts of gamma-hydroxybutyrate, wherein the mixture comprises a calcium salt of gamma-hydroxybutyrate, a magnesium salt of gamma-hydroxybutyrate, a potassium salt of gamma-hydroxybutyrate, and a sodium salt of gamma-hydroxybutyrate.

DETAILED DESCRIPTION

The present disclosure provides novel treatments for certain psychological disorders. More specifically, the present disclosure is directed to the treatment of anxiety disorders, obsessive-compulsive disorders, and trauma- and stressor-related disorders.

Anxiety Disorders include, but are not limited to, separation anxiety disorder, generalized anxiety disorder, social anxiety disorder, panic disorder, phobias (specific, agoraphobia), and selective mutism, among others.

Obsessive-Compulsive and Related Disorders (OCRD) include, but are not limited to, obsessive-compulsive disorder, body dysmorphic disorder, hoarding disorder, trichotillomania, and excoriation disorder.

Trauma- and stressor-related disorders include, but are not limited to, post-traumatic stress disorder (PTSD), reactive attachment disorder, disinhibited social engagement disorder, acute stress disorder, and adjustment disorder.

It is notable that decisions as to how disorders are categorized (such as via the DSM-5) relates to evidence of an underlying relationship between such disorders. Such a relationship may be evidenced by (i) symptom similarity, (ii) comorbidity, (iii) onset/presentation/progression of disorders, (iv) risk factors (genetic and environmental), (v) biological markers, (vi) treatment response, and (vii) neural substrates.

All of the aforementioned psychological disorders are treatable via methods presented herein.

As used herein, the term "gamma-hydroxybutyrate" (GHB) or "oxybate" refers to the negatively charged or anionic form of gamma-hydroxybutyric acid. GHB may have the following structure:

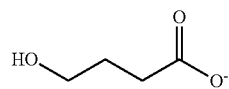

As described herein, gamma-hydroxybutyrate may also be referred to as 4-Hydroxybutanoate, 4-Hydroxy Butyrate, 4-hydroxybutyric acid, Acide 4-hydroxybutanoïque, Acide Gamma-Hydroxybutyrique, Acide Gamma-Hydroxy-Butyrique, Ecstasy Liquide, Gamma Hydrate, Gamma-Hydroxybutyrate, Gamma-Hydroxy-Butyrate, Gamma Hydroxy-Butyrate de Sodium, Gamma Hydroxybutyrate Sodium, Gamma Hydroxybutyric Acid, Gamma-Hidroxibutirato, Gamma-OH, Oxybate de Sodium, Oxybutyrate de Sodium, Sodium 4-hydroxybutyrate, Sodium gamma-hydroxybutyrate, Sodium Oxybate, or Sodium Oxybutyrate.

As used herein, the terms "gamma-hydroxybutyrate salt" or "gamma-hydroxybutyrate salts" refer to a compound formed by the interaction of gamma-hydroxybutyrate or gamma-hydroxybutyric acid (the conjugate acid of gamma-hydroxybutyrate) with a base, for example, NaOH, KOH, $Mg(OH)_2$, and $Ca(OH)_2$, and the like, the hydrogen atoms of the acid being replaced by the positive ion or cation of the base.

For example, "gamma-hydroxybutyrate sodium salt," which refers to the sodium salt form of gamma-hydroxybutyric acid (and is also known as "sodium gamma-hydroxybutyrate" or "sodium oxybate"), may have the following structure:

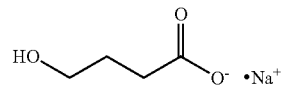

It will be understood by those skilled in the art that such salts may be in solid form, or such salts may be in partially or fully solvated form, for example, as when dissolved in an aqueous medium. It will be further understood by those skilled in the art, that, depending on the solubility of the salt in the aqueous medium, that the salt may be present in the aqueous medium as solvated cation(s) and anion(s), or as a precipitated solid.

In some embodiments, the cation or cations conjugated to gamma-hydroxybutyrate to form the one or more than one gamma-hydroxybutyrate salt may comprise, but are not limited to, aluminum, arginine, benzathine, calcium, chloroprocaine, choline, diethanolamine, ethanolamine, ethylenediamine, lysine, magnesium, histidine, lithium, meglumine, potassium, procaine, sodium, trimethylamine, or zinc.

Gamma-hydroxybutyrate salts useful in conjunction with embodiments of the invention may comprise one or more of: calcium oxybate, magnesium oxybate, potassium oxybate, sodium oxybate, or other combinations or conjugations of negatively charged gamma-hydroxybutyrate (gamma-hydroxybutyric acid) with any suitable inorganic or organic cation.

In some embodiments, the calcium oxybate is present in a wt/wt % of about 1% to about 5%, about 5% to about 10%, about 10% to about 15%, about 15% to about 20%, about 20% to about 25%, about 25% to about 30%, about 30% to about 35%, about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, about 90% to about 95%, or about 95% to about 100%. In some embodiments, the calcium oxybate is absent.

In some embodiments, the magnesium oxybate is present in a wt/wt % of about 1% to about 5%, about 5% to about 10%, about 10% to about 15%, about 15% to about 20%, about 20% to about 25%, about 25% to about 30%, about 30% to about 35%, about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, about 90% to about 95%, or about 95% to about 100%. In some embodiments, the magnesium oxybate is absent.

In some embodiments, the potassium oxybate is present in a wt/wt % of about 1% to about 5%, about 5% to about 10%, about 10% to about 15%, about 15% to about 20%, about 20% to about 25%, about 25% to about 30%, about 30% to about 35%, about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, about 90% to about 95%, or about 95% to about 100%. In some embodiments, the potassium oxybate is absent.

In some embodiments, the sodium oxybate is present in a wt/wt % of about 1% to about 5%, about 5% to about 10%, about 10% to about 15%, about 15% to about 20%, about 20% to about 25%, about 25% to about 30%, about 30% to about 35%, about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, about 90% to about 95%, or about 95% to about 100%. In some embodiments, the sodium oxybate is absent.

In some embodiments, the calcium oxybate is present in a wt/wt % of about 5% to about 40%, the magnesium oxybate is present in a wt/wt % of about 5% to about 30%, the potassium oxybate is present in a wt/wt % of about 10% to about 40%, and the sodium oxybate is present in a wt/wt % of about 5% to about 40%. In some embodiments, calcium oxybate, magnesium oxybate, potassium oxybate, sodium oxybate are present in respective wt/wt % ratios of about 47%:19%:26%:8%, at a total concentration of about 500 mg/mL.

In some embodiments, gamma-hydroxybutyrate may be substituted with a gamma-hydroxybutyrate analog. As used herein, gamma-hydroxybutyrate analogs may include, but are not limited to gamma-hydroxyvalerate, 3-methyl-GHB, 4-methyl-GHB, and 4-phenyl-GHB, and the like. One or more gamma-hydroxybutyrate salts may accordingly comprise one or more salts comprising gamma-hydroxybutyrate analog in place of gamma-hydroxybutyrate.

The terms "treat," "treating" or "treatment," as used herein and the appended claims, refer to reducing, alleviating or abrogating a disorder or disease and/or its attendant signs or symptoms.

The term "pharmaceutical composition" refers to a mixture of a compound, formulation or combination of compounds disclosed herein with other chemical components, such as diluents or carriers. The pharmaceutical composition facilitates administration of the compound or formulation to an organism. Multiple techniques of administering a compound or formulation exist in the art including, but not limited to, oral, injection, aerosol, parenteral, and topical administration. Pharmaceutical compositions can also be obtained by reacting compounds or formulations with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound or formulation.

The chemical compounds described herein can be administered to a human patient per se, or in pharmaceutical compositions where they are mixed with suitable carriers or excipient(s). Techniques for formulation and administration of the compounds of the instant application may be found in "Remington's Pharmaceutical Sciences," Mack Publishing Co., Easton, Pa., 18th edition, 1990 (incorporated herein by reference).

Suitable routes of administration may, for example, include oral, transmucosal, sublingual, transdermal, or topical administration. The compounds, compositions or formulation may also be administered in sustained or controlled release dosage forms, including depot injections, osmotic pumps, pills, transdermal patches, and the like, for prolonged and/or timed, pulsed administration at a predetermined rate.

The pharmaceutical compositions of the present invention may be manufactured in a manner that is itself known, e.g., by means of conventional mixing, dissolving, granulating, dragee-making, levigating, emulsifying, encapsulating, entrapping or tableting processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

For oral administration, the compounds can be formulated readily by combining the active compounds with pharmaceutically acceptable carriers well known in the art. Such carriers enable the compounds of the invention to be formulated as tablets, pills, dragée, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragée cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragée cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragée coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragée coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

All formulations for oral administration should be in dosages suitable for such administration.

The formulation or pharmaceutical preparations as described herein may be used to treat anxiety disorders (including panic disorder), obsessive-compulsive disorders, and trauma- and stressor-related disorders (notably but not exclusively PTSD) by administering to a subject in need thereof with a formulation or pharmaceutical composition or preparation as described herein.

For example, in one embodiment, treatment for PTSD or another of the aforementioned psychological disorders may comprise oral administration of a fixed dosage of the one or more than one gamma-hydroxybutyrate salts at regular intervals.

For example, dosage of the one or more than one gamma-hydroxybutyrate salt may be from 1 g to 10 g, or about 1 g, 2 g, 3 g, 4 g, 5 g, 6 g, 7 g, 8 g, 10 g, or any amount therebetween. The selected dosage may be once, twice, three times, or four times per day. Each dose may be taken in capsule form, or dissolved in water or another liquid carrier.

The present disclosure also relates to a method of treating PTSD or other psychological disorder by administering to a subject in need thereof the formulation or pharmaceutical composition or preparation as described above over a treatment period. The treatment may be for a period of time or may be continuous.

Additional details regarding the aforementioned pharmaceutical compositions, including examples of compositions of gamma-hydroxybutyrate salts, examples of aqueous solutions of gamma-hydroxybutyrate salts, formulations of gamma-hydroxybutyrate salts, dosing, methods of making/synthesis of gamma-hydroxybutyrate salts, can be found in U.S. Pat. No. 8,591,922B1, U.S. Pat. No. 9,132,107B2, U.S. Pat. No. 8,901,173B2, U.S. Ser. No. 10/195,168B2, and U.S. Ser. No. 10/675,258B2, previously referenced and incorporated herein by reference.

EXAMPLE(S)

These and other features of the present invention will be made apparent from the following example(s). The following example(s), as described, are not intended to be construed as limiting the scope of the present invention.

It will be readily understood by the skilled artisan that numerous alterations may be made to the examples and instructions given herein. For example, alterations may be made to the purification and formulation of gamma-hydroxybutyrate or one or more than one gamma-hydroxybutyrate salts.

Efficacy Study. Table 1 below demonstrates that pharmaceutical compositions comprising gamma-hydroxybutyrate salts are useful for treating symptoms of psychological disorders mentioned herein. A female patient exhibiting symptoms of various psychological disorders was treated with 2.25 g of mixed, gamma-hydroxybutyrate salts (XYWAV® brand oral solution of calcium, magnesium, potassium, and sodium oxybates, available from Jazz Pharmaceuticals of Dublin, Ireland) diluted in 60 ml of water, orally administered, twice daily, once at bedtime, and the second dose 4 hours later. The pre- and post-treatment results are the patient's subjective evaluation of the severity of her symptoms on a scale of 0 to 10, wherein a "0" is indicative of no symptoms, and a "10" is indicative of maximally severe symptoms. Post treatment results were observed as indicated after 3 weeks of treatment.

TABLE 1

| Disorder | Prior to Treatment | Post Treatment |
| --- | --- | --- |
| PTSD | 10 | 3 |
| Panic disorder | 8 | 2 |
| Anxiety disorder | 9 | 2 |

In one example, a dosage for treatment of psychological disorders comprises oral administration of 3.0 g of a mixture of gamma-hydroxybutyrate salts diluted in 60 ml of water twice daily: once at bedtime and then after at least 2 hours and up to 4 hours with no intake of food or beverages. The mixture of gamma-hydroxybutyrate salts includes calcium oxybate, magnesium oxybate, potassium oxybate, and sodium oxybate present in respective wt/wt % ratios of about 47%:19%:26%:8%, at a total concentration of about 500 mg/mL. Improvement of anxiety and signs and symptoms of PTSD were observed after approximately four (4) weeks of treatment.

The present invention has been described with regard to one or more embodiments. However, it will be apparent to persons skilled in the art that a number of variations and modifications can be made without departing from the scope of the invention as defined in the claims.

What is claimed is:

1. A method of treating a patient having a psychological disorder, wherein the psychological disorder is post-traumatic stress disorder, the method comprising administering to the patient an effective amount of a pharmaceutical composition comprising a mixture of calcium oxybate, magnesium oxybate, potassium oxybate, an sodium oxybate, wherein the calcium oxybate is present in a wt/wt % of about 5% to about 40%, the magnesium oxybate is present in a wt/wt % of about 5% to about 30%, the potassium oxybate is present in a wt/wt % of about 10% to about 40%, and the sodium oxybate is present in a wt/wt % of about 5% to about 40%.

2. The method of claim 1, wherein the pharmaceutical composition is orally administered.

3. A method of treating a patient having a psychological disorder, wherein the psychological disorder is post-traumatic stress disorder, the method comprising orally administering to the patient a pharmaceutical composition comprising a mixture of four salts of gamma-hydroxybutyrate, wherein the mixture comprises a calcium salt of gamma-hydroxybutyrate, a magnesium salt of gamma-hydroxybutyrate, a potassium salt of gamma-hydroxybutyrate, and a sodium salt of gamma-hydroxybutyrate, and wherein the salts are present in a wt/wt % ratio of about 47%:19%:26%:8%, respectively.

* * * * *